United States Patent [19]

Mentrup et al.

[11] 3,975,525

[45] Aug. 17, 1976

[54] N-[4'-IMIDAZOLIDINON-(2)-YL-PHENETHYL]-N'-PYRIDYL-PIPERAZINES AND SALTS THEREOF

[75] Inventors: Anton Mentrup; Ernst-Otto Renth; Kurt Schromm, all of Ingelheim am Rhein; Peter Danneberg, Ockenheim, all of Germany

[73] Assignee: Boehringer Ingelheim GmbH, Ingelheim am Rhein, Germany

[22] Filed: Dec. 1, 1975

[21] Appl. No.: 636,740

Related U.S. Application Data

[63] Continuation-in-part of Ser. No. 440,823, Feb. 8, 1974, Pat. No. 3,937,708, which is a continuation of Ser. No. 259,532, June 5, 1972, abandoned.

[30] Foreign Application Priority Data

June 7, 1971 Austria ................ 4920123/71

[52] U.S. Cl. .................. 424/250; 260/268 H
[51] Int. Cl.² ............ C07D 401/14; A61K 31/495
[58] Field of Search ............... 424/250; 260/268 H

[56] References Cited
UNITED STATES PATENTS 3,937,708    2/1976    Mentrup et al. ............ 260/268 PH Primary Examiner—Nicholas S. Rizzo
Assistant Examiner—Jose Tovar
Attorney, Agent, or Firm—Hammond & Littell

[57] ABSTRACT

Compounds of the formula

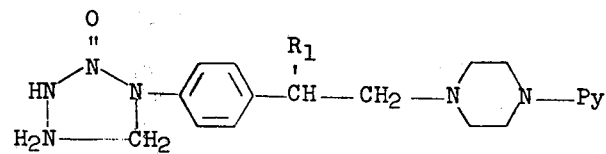

wherein $R_1$ is hydrogen or hydroxyl, and Py is pyridyl, and non-toxic, pharmacologically acceptable acid addition salts thereof; the compounds as well as the salts are useful as CNS-depressants, neuroleptics and anti-cholesteremics.

5 Claims, No Drawings

N-[4'-IMIDAZOLIDINON-(2)-YL-PHENETHYL]-N'-PYRIDYL-PIPERAZINES AND SALTS THEREOF

This is a continuation-in-part of copending application Ser. No. 440,823 filed Feb. 8, 1974 now U.S. Pat. No. 3,937,708, issued Feb. 10, 1976; which in turn is a continuation of application Ser. No. 259,532 filed June 5, 1972, now abandoned.

This invention relates to novel N-[4'-imidazolidinon-(2)-yl-phenethyl]-N-pyridyl-piperazines and acid addition salts thereof, as well as to methods of preparing these compounds.

More particularly, the present invention relates to a novel class of compounds represented by the formula

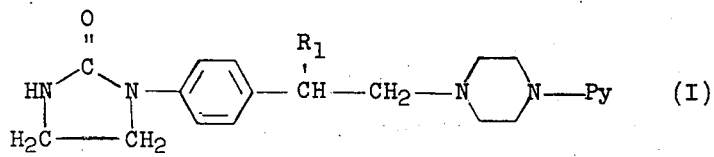

wherein $R_1$ is hydrogen or hydroxyl, and

Py is pyridyl, preferably 2-pyridyl, and non-toxic, pharmacologically acceptable acid addition salts thereof.

The compounds embraced by formula I above may be prepared by the following methods:

Method A

For the preparation of a compound of the formula I wherein $R_1$ is hydroxyl, by reducing a ketone of the formula

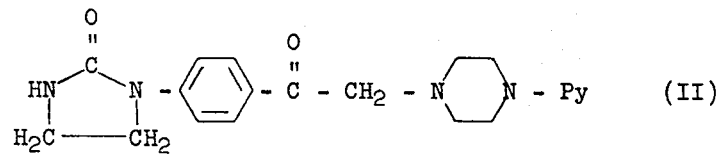

wherein Py has the same meanings as in formula I, preferably with a complex hydride such as sodium borohydride, or also with catalytically activated hydrogen.

Method B

For the preparation of a compound of the formula I wherein $R_1$ is hydrogen, by subjecting an ethylenediamine derivative of the formula

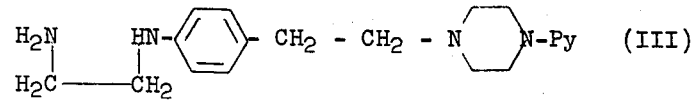

wherein Py has the same meanings as in formula I, to ring closure with a suitable carbonic acid derivative, especially with phosgene, a chlorocarbonic acid ester, a carbonic acid ester, N,N'-carbonyl-diimidazole or urea, or with a metal cyanate in the presence of an acid.

However, instead of starting from a diamine of the formula III, it is also possible to start from an intermediate, such as a carbamate, a urea or a carbamic acid chloride, and subject it to ring closure.

The starting compounds needed for methods A and B are either known compounds or may be prepared by conventional methods.

The compounds embraced by formula I occur as racemic mixtures or as optically active isomers, such as antipode pairs or diastereomeric pairs; to the extent that these compounds occur as racemates or diastereomeric antipode pairs, these may be separated in conventional manner into the diastereomeric racemates or the individual optical antipodes.

The optically inactive as well as the optically active forms of the compounds of the formula I are organic bases and therefore form acid addition salts with inorganic or organic acids. Examples of non-toxic, pharmacologically acceptable acid addition salts are those formed with hydrochloric acid, hydrobromic acid, sulfuric acid, methanesulfonic acid, acetic acid, propionic acid, citric acid, maleic acid, tartaric acid, 8-chlorotheophylline or the like.

The following examples illustrate the present invention and will enable others skilled in the art to understand it more completely. It should be understood, however, that the invention is not limited solely to the particular examples given below.

EXAMPLE 1

N-[1-(4'-Imidazolidinon-(2)-yl-phenyl)-1-hydroxyethyl]-N'-(2''-pyridyl)-piperazine 14.15 gm of 4-[imidazolidinon-(2)-yl]-ω-bromoacetophenone (m.p. 175°C) were refluxed with 16.3 gm of N-(α-pyridyl)-piperazine in 150 ml of acetonitrile for 45 minutes. After separation of the precipitated N-(α-pyridyl)-piperazine hydrobromide, the compound of the formula

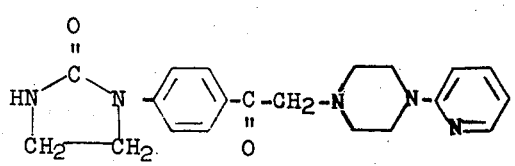

was isolated as the base (76% of theory); m.p. 214°C (from ethanol).

Reduction of this ketone with NaBH₄ in 90% methanol resulted in the corresponding hydroxyl compound with a yield of 88.5%; m.p. 218°C (from ethanol).

EXAMPLE 2

N-[4'-Imidazolidinon-(2)-yl-phenethyl]-N'-(2''-pyridyl)-piperazine 14.1 gm of N-(4-aminophenethyl)-N'-(2'-pyridyl)-piperazine, 1.6 gm of paraformaldehyde and a solution of 4.1 gm of potassium cyanide in 7 ml of water were combined in 85 ml of glacial acetic acid at 15° to 20°C, and the reaction was allowed to go to completion by leaving the reaction mixture to stand overnight at room temperature. The resulting cyanomethylamino-compound was hydrogenated to the corresponding ethylene-diamino derivative with hydrogen in methanol, using PtO₂ as the catalyst. The calculated quantity of N,N'-carbonyl diimidazole, dissolved in tetrahydrofuran, was added to this ethylenediamino derivative in benzene. The reaction mixture was left to stand overnight at room temperature and was then refluxed for 2 hours, yielding the compound of the formula

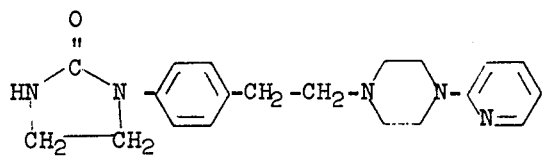

which was isolated as the base; m.p. 200°C.

The compounds according to the present invention, that is, those embraced by formula I and their non-toxic, pharmacologically acceptable acid addition salts, in both the optically inactive and optically active forms, have useful pharmacodynamic properties. More particularly, the compounds of the present invention exhibit CNS-depressing, neuroleptic and anti-cholesteremic activities in warm-blooded animals, such as mice, rats, guinea pigs, dogs and cats.

For pharmaceutical purposes the compounds according to the present invention are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, aerosols, suppositories and the like. One effective dosage unit of the compounds according to the present invention is from about 0.026 to 1.35 mgm/kg body weight, preferably from 0.066 to 0.67 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 3

Tablets

The tablet composition is compounded from the following ingredients:

| | |
|---|---:|
| N-[4'-Imidazolidinon-(2)-yl-phenethyl]-N'-(2''-pyridyl)-piperazine | 30 parts |
| Lactose | 70 parts |
| Corn starch | 93 parts |
| Secondary calcium phosphate | 47 parts |
| Soluble starch | 3 parts |
| Magnesium stearate | 3 parts |
| Colloidal silicic acid | 4 parts |
| Total | 250 parts |

Preparation:

The piperazine compound is intimately admixed with the lactose, the corn starch and the calcium phosphate, the mixture is granulated with the aid of an aqueous solution of the soluble starch in conventional fashion, and the granulate is dried and admixed with the remaining ingredients. The composition is compressed into 250 mgm-tablets in a conventional tablet making machine. Each tablet contains 30 mgm of the piperazine compound and is an oral dosage unit composition with effective CNS-depressing action.

EXAMPLE 4

Coated pills

The pill core composition is compounded from the following ingredients:

| | |
|---|---:|
| N-[1-(4'-Imidazolidinon-(2')-yl-phenyl)-1-hydroxy-ethyl]-N'-(2''-pyridyl)-piperazine | 40 parts |
| Lactose | 50 parts |
| Corn starch | 80 parts |
| Secondary calcium phosphate | 50 parts |
| Magnesium stearate | 3 parts |
| Soluble starch | 3 parts |
| Colloidal silicic acid | 4 parts |
| Total | 230 parts |

Preparation:

The ingredients are compounded in the same manner as in the preceding example, the composition is compressed into 230 mgm-pill cores which are subsequently coated with a thin shell consisting essentially of a mixture of talcum, sugar and gum arabic, and the coated pills are polished with beeswax. Each pill contains 40 mgm of the piperazine compound and is an oral dosage unit composition with effective CNS-depressing action.

EXAMPLE 5

Suppositories

The suppository composition is compounded from the following ingredients:

| | |
|---|---:|
| N-[4'-Imidazolidinon-(2)-yl-phenethyl]-N'-(2''-pyridyl)-piperazine | 30 parts |
| Lactose, powdered | 45 parts |
| Suppository base (e.g. cocoa butter) | 1625 parts |
| Total | 1700 parts |

Preparation:

The lactose and the piperazine compound are intimately admixed with each other, the mixture is homogeneously blended into the molten suppository base, and 1700 mgm-portions of the composition are filled into cooled suppository molds and allowed to harden therein. Each suppository contains 30 mgm of the piperazine compound and is a rectal dosage unit composition with effective CNS-depressing action.

Analogous results are obtained when any one of the other N-phenyl-imidazolidinones embraced by formula I or a non-toxic salt thereof was substituted for the particular N-phenyl-imidazolidinone in Examples 3 through 5. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

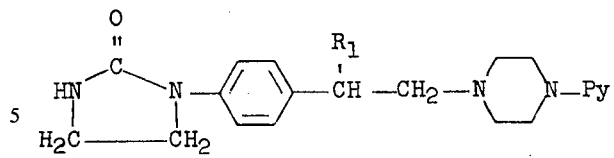

wherein $R_1$ is hydrogen or hydroxyl, and Py is pyridyl, or a non-toxic, pharmacologically acceptable acid addition salt thereof.

2. A compound of claim 1, which is N-[1-(4'-imidazolidinon-(2)-yl-phenyl)-1-hydroxy-ethyl]-N'-(2''-pyridyl)-piperazine or a non-toxic, pharmacologically acceptable acid addition salt thereof.

3. A compound of claim 1, which is N-[4'-imidazolidinon-(2)-yl-phenethyl]-N'-(2''-pyridyl)-piperazine or a non-toxic, pharmacologically acceptable acid addition salt thereof.

4. A pharmaceutical dosage unit composition consisting essentially of an inert pharmaceutical carrier and an effective CNS-depressing amount of a compound of claim 1.

5. The method of depressing the central nervous system of a warm-blooded animal in need of such treatment, which comprises perorally or parenterally administering to said animal an effective CNS-depressing amount of a compound of claim 1.

* * * * *